(12) United States Patent
Davis, III

(10) Patent No.: US 8,639,702 B2
(45) Date of Patent: Jan. 28, 2014

(54) SYSTEM AND METHOD TO CLASSIFY AND APPLY BEHAVIORAL STIMULI POTENTIALS TO DATA IN REAL TIME

(75) Inventor: Charles F. L. Davis, III, Lynbrook, NY (US)

(73) Assignee: BehaviorMatrix, LLC, Blue Bell, PA (US)

( * ) Notice: Subject to any disclaimer, the term of this patent is extended or adjusted under 35 U.S.C. 154(b) by 0 days.

(21) Appl. No.: 13/315,602

(22) Filed: Dec. 9, 2011

(65) Prior Publication Data

US 2012/0150872 A1  Jun. 14, 2012

Related U.S. Application Data

(60) Provisional application No. 61/422,001, filed on Dec. 10, 2010.

(51) Int. Cl.
*G06F 17/30* (2006.01)

(52) U.S. Cl.
USPC .......................................................... 707/748

(58) Field of Classification Search
USPC .......................................................... 707/748
See application file for complete search history.

(56) References Cited

U.S. PATENT DOCUMENTS

| | | | |
|---|---|---|---|
| 7,401,057 B2 | 7/2008 | Eder | |
| 7,571,146 B2 | 8/2009 | Dalton | |
| 7,689,432 B2 | 3/2010 | Gross | |
| 7,801,842 B2 | 9/2010 | Dalton | |
| 7,917,458 B2 | 3/2011 | Dalton | |
| 2002/0091654 A1* | 7/2002 | Alroy | 706/21 |
| 2008/0270426 A1 | 10/2008 | Flake et al. | |
| 2008/0270473 A1 | 10/2008 | Flake et al. | |
| 2008/0270474 A1 | 10/2008 | Flake et al. | |
| 2008/0270476 A1 | 10/2008 | Flake et al. | |
| 2008/0270551 A1 | 10/2008 | Flake et al. | |
| 2008/0270615 A1 | 10/2008 | Centola et al. | |
| 2008/0270620 A1 | 10/2008 | Flake et al. | |
| 2009/0030772 A1 | 1/2009 | Flake et al. | |
| 2009/0089078 A1* | 4/2009 | Bursey | 705/1 |
| 2009/0306741 A1 | 12/2009 | Hogle | |
| 2009/0312817 A1* | 12/2009 | Hogle et al. | 607/54 |
| 2010/0077261 A1 | 3/2010 | Jung | |
| 2010/0280988 A1 | 11/2010 | Underkoffler | |
| 2012/0023103 A1* | 1/2012 | Soderberg et al. | 707/739 |

FOREIGN PATENT DOCUMENTS

| | | | | |
|---|---|---|---|---|
| WO | 2010/085156 | * | 7/2010 | 707/739 |
| WO | WO 2010085186 A1 | * | 7/2010 | |

* cited by examiner

*Primary Examiner* — Pierre Vital
*Assistant Examiner* — Courtney Harmon
(74) *Attorney, Agent, or Firm* — Gregory J. Winsky; Jason F. Cotter; Archer & Greiner, P.C.

(57) ABSTRACT

A system and method for digitally classifying and analyzing exposure to behavioral influencers to probabilistically determine behaviors likely to be demonstrated by an individual or cohorts of individuals based on a combination of demographic and psychographic attributes. The system and method transforms raw data into useful data elements having associated exteroceptive values and other metadata that is useful for further evaluation, analysis, integration into a model, or other behavioral data utilization.

21 Claims, 4 Drawing Sheets

SYSTEM AND METHOD TO CLASSIFY AND APPLY BEHAVIORAL STIMULI POTENTIALS TO DATA IN REAL TIME

CROSS REFERENCE TO RELATED APPLICATION(S)

This application claims the benefit of U.S. Provisional Application No. 61/422,001, filed Dec. 10, 2010, the disclosure of which is incorporated herein in its entirety.

FIELD OF THE INVENTION

The present invention relates in general to systems and methods for executing computational processes as they relate to behavioral analytics.

BACKGROUND OF THE INVENTION

A data element forms the premise on which an inference may be drawn and represents the lowest level of abstraction from which information and then knowledge are derived. In humans, the perception of environment or condition is comprised of data gathered by the senses, i.e., the physiological capacity to provide input for perception. These "senses" are formally referred to as the exteroceptive senses and in humans comprise quantifiable or potential sensory data including, sight, smell, hearing, touch, taste, temperature, pressure, pain, and pleasure, the admixture of which determine the spectrum of human emotion states and resultant behaviors.

Potentials in these senses work independently, or in combination, to produce unique perceptions. For instance, the sense of sight is primarily used to identify a food item, but the flavor of the food item incorporates the senses of both taste and smell.

In biological terms, behavior can generally be regarded as any action of an organism that changes its relationship to its environment. Definable and measurable behaviors are predicated on the association of stimuli within the domain of exteroceptive sensation, to perception, and ultimately, a behavioral outcome.

The ability to determine the exteroceptive association and impact on behavior from data that is not physical but exists only in digital form has profound implications for how data is viewed, both intrinsically and associatively.

An advantage exists, therefore, for a system and method for dynamically associating digital data with values that approximate exteroceptive stimuli potentials, and from those values forecasting probabilistically the likely behavioral response to that data, thereby promoting the ability to design systems and models to predict behavioral outcomes that are inherently more accurate in determining behavioral response. In turn, interfaces and computing devices may be developed that would "expect" certain behaviors, or illicit them through the manipulation of data. Additionally, models could be constructed to classify data not only for the intrinsic value of the data but for the potential behavioral influence inherent in the data as well.

SUMMARY OF THE INVENTION

The present invention achieves the foregoing objectives by providing a system and method for digitally classifying and analyzing exposure to behavioral influencers to probabilistically determine behaviors likely to be demonstrated by an individual or cohorts of individuals based on a combination of demographic and psychographic attributes.

Other details, objects and advantages of the present invention will become apparent as the following description of the presently preferred embodiments and presently preferred methods of practicing the invention proceeds.

BRIEF DESCRIPTION OF THE DRAWINGS

The invention will become more readily apparent from the following description of preferred embodiments thereof shown, by way of example only, in the accompanying drawings wherein.

DETAILED DESCRIPTION OF THE INVENTION

Figure 1:
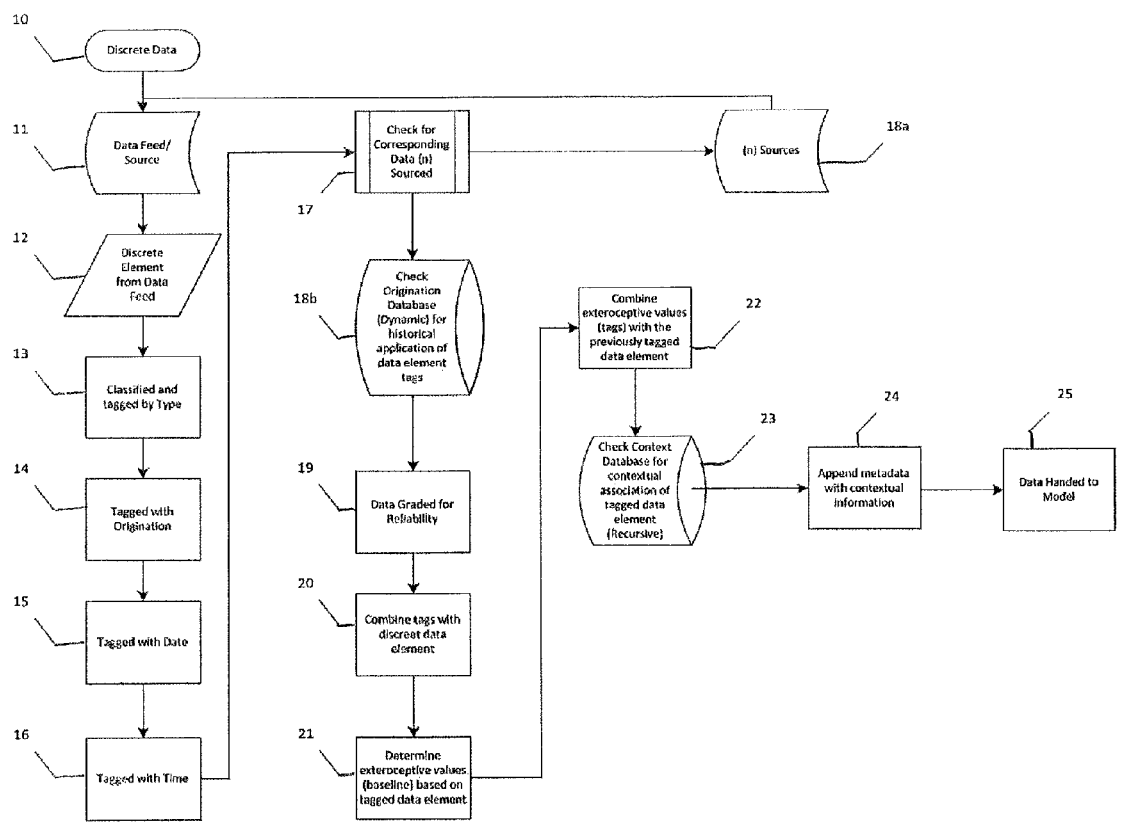
FIG. 1 is a flow diagram of a process according to the present invention.

Referring to the drawings, in FIG. 1 there is generally shown a process flow diagram whereby disparate raw data or data elements 10 is collected and organized in whole or in part via sensor(s) to measure physical conditions such as temperature, or through the systematic incorporation or "digital scraping", to constitute an external data feed or organized source of data 11.

Discrete data elements 12 derived from the feed are processed based on the structural and organizational characteristics of the originating feed itself. More particularly, the system determines whether the feed consists of a single text message document, or is part of a collection of such documents, or a stream of data from a website, or from a sensor or array of sensors. The data is then classified (tagged) with associative metadata according to type 13, origination 14, date 15 and time 16.

A test of data integrity 17 is conducted by looking for alternate "(n)" sources at 18a to confirm values for data that has been subject to the instant process and if those values are evident in single or multiple feeds.

Following the data integrity test, a dynamic origination database 18b compares previous data element tag interactions with the present data under consideration.

At 19, data is assessed for reliability and, at 20, all previous tagging is combined with the data element value. At 21, the data element is evaluated against a normative table of exteroceptive values to determine the appropriate exteroceptive value(s) to be attributed to the data element, which values are then associated with the data element at 22. Reference 23 illustrates the step of accessing a database of contextual information from previous data interactions. And, at 24, contextual information is appended with the metadata for the initial discrete data element, which process is preferably performed recursively to strengthen the contextual association to the data. At 25, the literal data value and its associative metadata are then transferred, as appropriate, for additional processing or modeling.

Referring to FIG. 1 in somewhat greater detail, it is seen that discrete and disparate data 10 is assembled and organized into various external repositories in a recurring manner. The discrete data 10 can be of any source and type, including but not limited to SMS or MMS text message documents, emails, web based feeds, and social media. According to the invention, at the moment when data is first encountered by the system, the data is considered to be absolute and immutable. However, a subsequent iteration of the feed (discussed below) may result in an update of the feed which might be different from the originally encountered feed, whereby the updated feed is treated as a discrete form of the initial feed. A repository of such discrete, associated data is considered to be a data feed and/or source 11 based on any number of criteria or specification. Such criteria might include locales from which the data feeds originate, or language. Discrete elements 12 of the data feed are then examined and sorted at 13 according to type such as, for example, web page content, social media status update, news report, or the like.

The data is assigned associative information, i.e., meta-tagged, that identifies origin 14, as well as temporal information including date of integration 15 and time of integration 16. As indicated at 17, in order to determine the validity of the data an attempt is made to identify corroborating sources or data feeds 18a. More particularly, to determine the validity of the data and to measure the variance of the data as represented across various data feeds, multiple feeds are sourced at 18a and evaluated. If the data is unrecognized, the process of examination and meta-tagging of discrete data is repeated, thereby resulting in an updated, discrete form of the initial feed which is also stored at 18a.

At 18b, an origination database is queried for past instances of similar data feed sourcing results. That is, an origination database of historical results of previous data tagging sessions 18b is consulted to determine validity of the data based on past data feed metatag usage. At 19, the data is then evaluated and tagged for reliability as well as a calculated rate of decay with regard to relevance.

At 20, the tagging from step 19 is then appended to the existing metadata for the data element. In other words, all meta-tags are then combined with the discrete data element to form a union of discrete data element and associated metadata.

The value of the data element and the associated metadata, is compared against a normative table of exteroceptive values and a new value of affective potential is calculated and assigned to the data element at 21. For example, the data element may be, but is not limited to, a social media status update whereby an individual transmits via a text message: "I'm eating pizza and it is delicious". This entry would be evaluated as stimulating the exteroceptive senses of sight, smell, taste, and temperature, with a behavioral bias toward encouraging hunger/desire in the viewer of the status update. The strength of the desire is further affected by the historical data of such references when evaluated against environmental conditions such as time and location.

The exteroceptive values are based on stimuli potentials necessary for human perception and cognition and are regarded to be precursors to a behavioral response when encountered. At 22, the exteroceptive values are combined with the previous metadata associated with the discrete data element to form an updated rendition of the metadata that incorporates all previous metadata values.

A database 23 of contextual observations is then accessed to determine the context of the exteroceptive values to the discrete data element and to assign appropriate contextual metadata to the data element. That is, a historical database 23 of previous classifications is queried for any contextual association that might be determined by the combined metadata values that are associated with the discrete data element. At 24, the contextual metadata is combined with the previously existing discrete data element metadata such that any contextual proximity is reflected in an updated amending of the metadata values associated with the discrete data element. At this point the process of behavioral analysis is considered complete whereby the discrete data element is now deemed to be rendered to possess the property of exteroception. Finally, the transformed data element is transferable, at 25, for further evaluation, analysis, integration into a predictive model, or other behavioral data utilization as may be desired.

Figure 2:
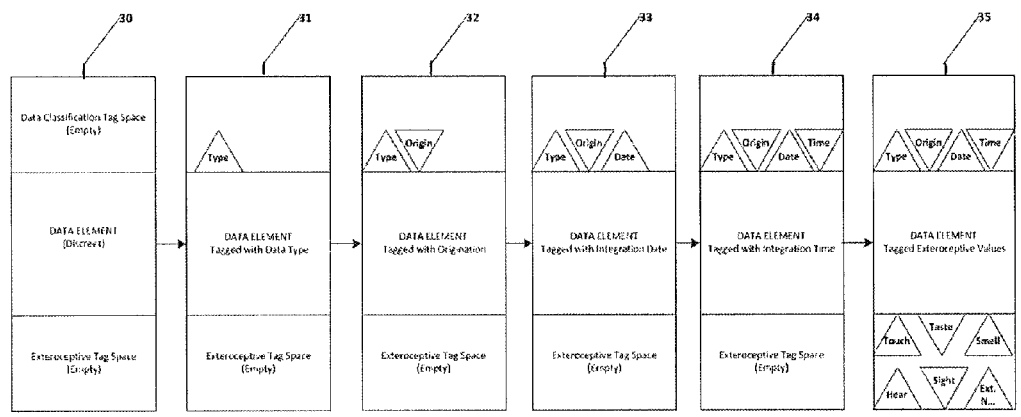
FIG. 2 is a flow diagram depicting transformation of a discrete data element to one that is altered by the invention to include associated exteroceptive metadata.

Referring now to FIG. 2, there is shown a data-centric flow diagram which graphically illustrates the progression and transformation of a discrete data element according to the present invention, i.e., into one that incorporates class, temporal, and exteroceptive values while preserving the original discrete value. At 30, a discrete data element is identified and allocation is made for classification by the initialization of a data repository (either internal or external) to store associative metadata. Data is first tagged by type at 31, subsequently tagged by origin at 32, integration date at 33 and integration time at 34. At 35, exteroceptive values are assigned as well to form an integrated meta-exteroceptive representation of the original data.

Figure 3:
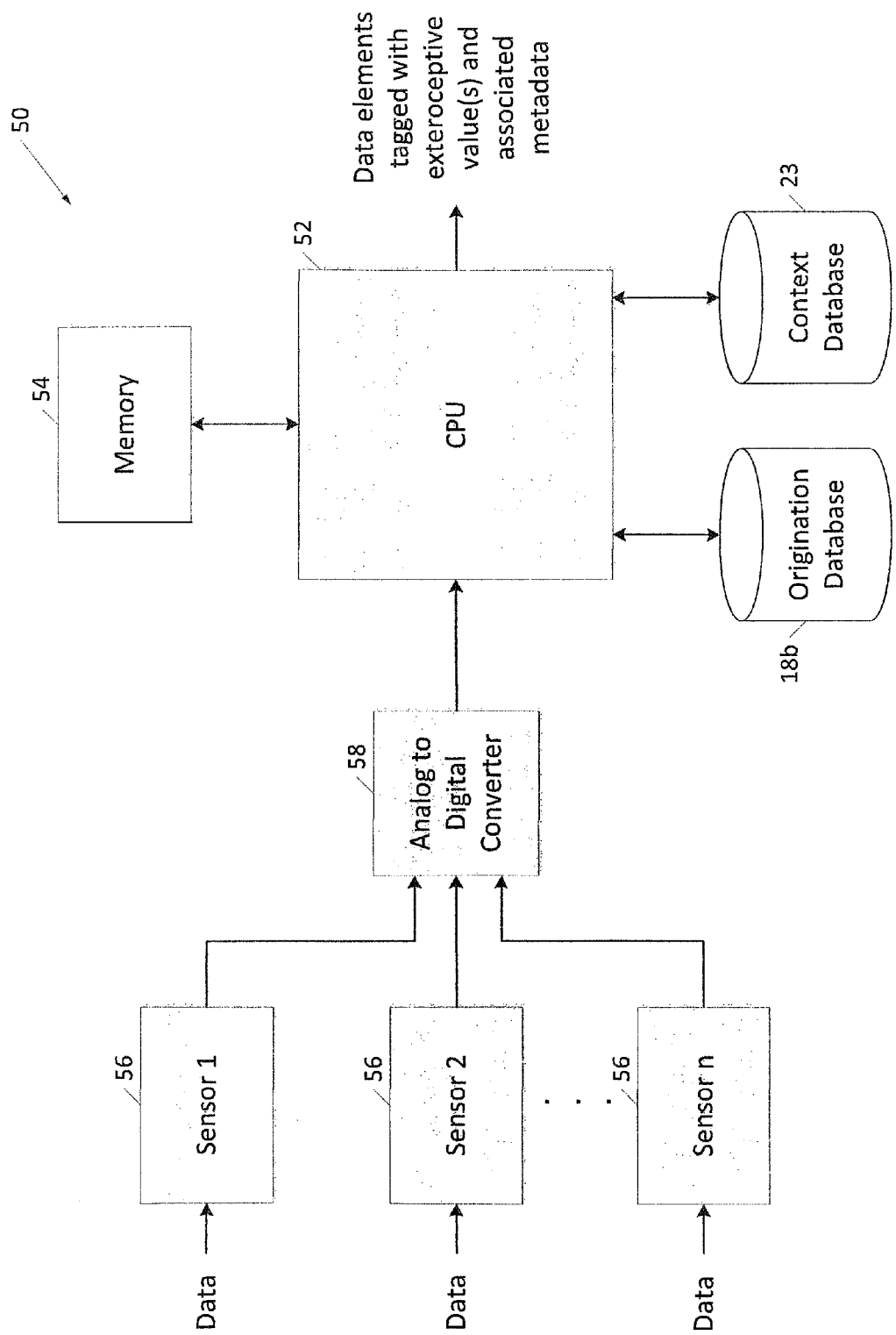
FIG. 3 depicts a system for carrying out the processes of the present invention.

FIG. 3 is representative of a computer system for carrying out an embodiment of the processes of the present invention. The system, identified generally by reference numeral 50, includes at least one microprocessor or central processing unit (CPU) 52 coupled to memory 54. System 50 may be a single computer or may be a distributed system of computers including a plurality of processors. In this regard, a distributed system of computers may include, without limitation, a local area network (LAN), a wide area network (WAN), a cloud-based system or any other arrangement of computers presently known or hereinafter developed. Likewise, memory 54 may be a single memory device or multiple components capable of cooperating to store executable programming necessary to implement the methods according to the invention. Suitable memory devices may include any portable, on-board or remote computer readable storage media known in the art such as, for example, optical media, magnetic media, solid state storage, grapheme or quantum dots, and storage area networks.

Continuing, system 50 includes data harvesting means in the form of one or more sensors 56 capable of detecting one or data elements including, without limitation, temperature, pressure, light, sound, motion, distance and time. The data signals received by sensor(s) 56 are converted by an analog-to-digital (A/D) converter 58 whereby the signals may be transmitted to and processed by CPU 52. Pursuant to the instructions stored in memory 54, CPU 52 sorts the incoming data into data feeds or sources from which discrete elements are tagged by type, origination, date and time, and checked for corresponding data sources.

The instructions stored in memory 54 then direct the CPU 52 to call origination database 18b to search for historical application of data element tags, grade the reliability of the data, combine metadata with discrete data elements, determine exteroceptive values based on the tagged data element, and then combine the exteroceptive values with the previously tagged data element. Thereafter, the instructions direct the CPU to recursively call the context database 23 for contextual association of the tagged data element and thereafter append the contextual metadata to the data element at 24 whereby the result is a transformed data element that is tagged with exteroceptive value(s) and associated metadata suitable, at 25, for evaluation, analysis, modeling, processing and/or other behavioral data utilization as may be desired.

Figure 4:
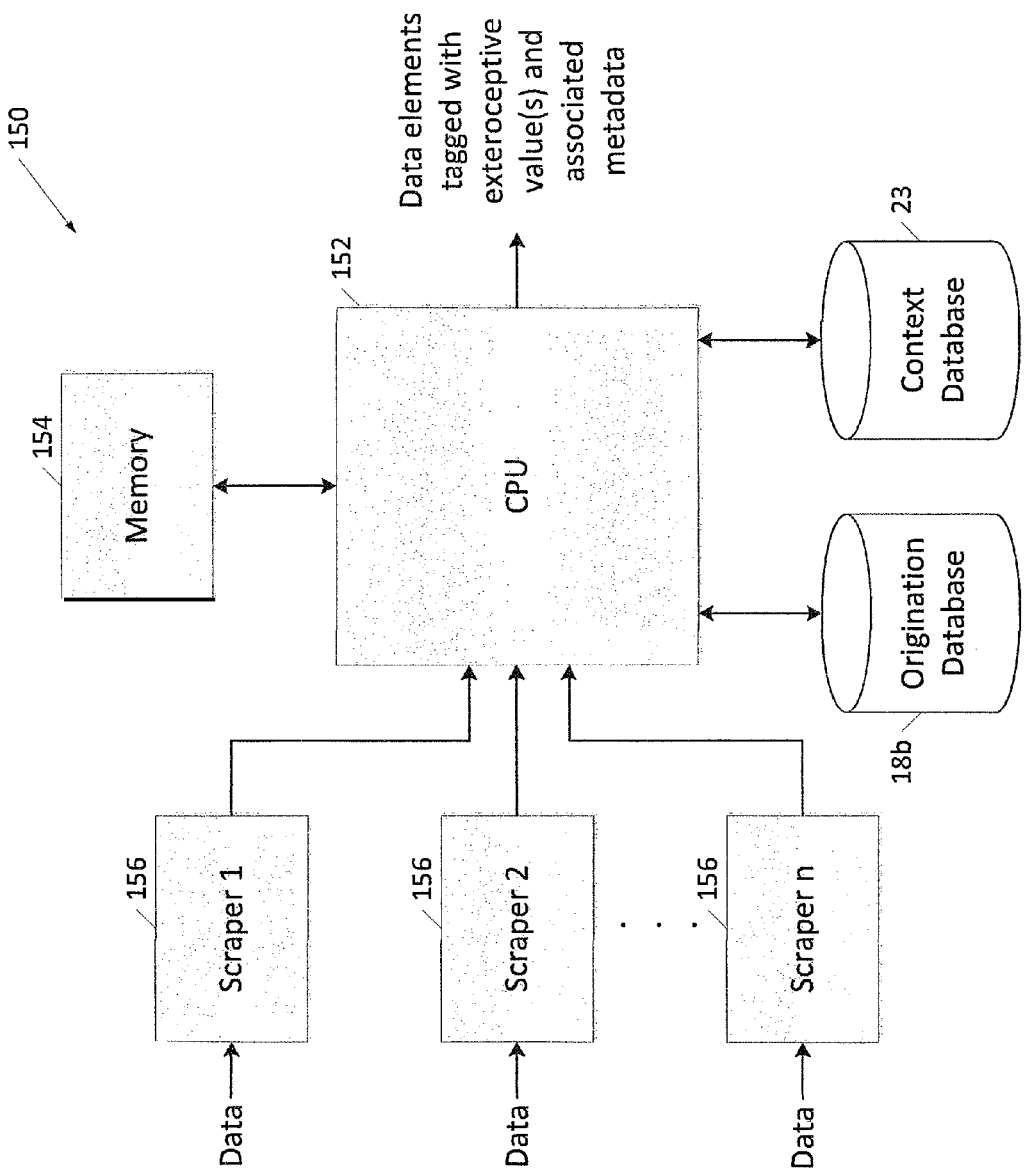
FIG. 4 depicts a further system for carrying out the processes of the present invention.

FIG. 4 is representative of a further embodiment of a computer system for carrying out the processes of the present invention. The system, identified generally by reference numeral 150, includes at least one microprocessor or central processing unit (CPU) 152 coupled to memory 154. System 150 may be a single computer or may be a distributed system of computers including a plurality of processors. In this regard, a distributed system of computers may include, without limitation, a local area network (LAN), a wide area network (WAN), a cloud-based system or any other arrangement of computers presently known or hereinafter developed. Likewise, memory 154 may be a single memory device or multiple components capable of cooperating to store executable programming necessary to implement the methods according to the invention. Suitable memory devices may include any portable, on-board or remote computer readable storage media known in the art such as, for example, optical media, magnetic media, solid state storage, graphene or quantum dots, and storage area networks.

Continuing, system 150 includes data harvesting means in the form of one or more digital media scrapers 156 capable of detecting one or more data elements including, without limitation, any digital data including text, graphics, audio and/or video file of any format. The data collected by the scraper(s) 156 are transmitted to and processed by CPU 152. Pursuant to the instructions stored in memory 154, CPU 152 sorts the incoming data into data feeds or sources from which discrete elements are tagged by type, origination, date and time, and checked for corresponding data sources.

The instructions stored in memory 154 then direct the CPU 152 to call origination database 18b to search for historical application of data element tags, grade the reliability of the data, combine metadata with discrete data elements, determine exteroceptive values based on the tagged data element, and then combine the exteroceptive values with the previously tagged data element. Thereafter, the instructions direct the CPU to recursively call the context database 23 for contextual association of the tagged data element and thereafter append the contextual metadata to the data element at 24 whereby the result is a transformed data element that is tagged with exteroceptive value(s) and associated metadata suitable, at 25, for evaluation, analysis, modeling, processing and/or other behavioral data utilization as may be desired.

Broadly, the present invention provides a system and method for inferring and assigning exteroceptive values to a data element so that the data element can be measured and evaluated for the ability to influence behavior. The advantages of the present invention include, without limitation, the ability to automatically assign exteroceptive stimuli potentials to disparate data in real-time.

While the foregoing written description of the invention enables one of ordinary skill to make and use what is considered to be the best mode thereof, those of ordinary skill will understand and appreciate the existence of variations, combinations, and equivalents of the specific embodiments, methods, and examples herein. The invention should therefore not be construed to be limited by the above described embodiments, methods, and examples, but by all embodiments and methods within the scope and spirit of the invention as claimed herein.

What is claimed is:

1. A system for transforming raw data into data elements having associated exteroceptive values, said system comprising:
   a microprocessor coupled to a memory, said memory storing programming for controlling said microprocessor;
   data harvesting means in communication with said microprocessor for receiving discrete data elements;
   a first database in communication with said microprocessor; and
   a second database in communication with said microprocessor,
   wherein said microprocessor is instructed by said programming to:
   receive discrete data elements from said data harvesting means;
   organize said data elements into at least one data feed;
   assign first metadata to said data elements;
   test data integrity by searching for an alternate number of sources in order to confirm said first metadata;
   access said first database to determine the validity of said data elements based on past data feed metatag usage;
   assign reliability metadata to said data elements;
   combine said reliability metadata with said first metadata;
   assign exteroceptive values to said data elements based on values of said data elements, said reliability metadata and said first metadata;
   combine said exteroceptive values with said reliability metadata and said first metadata;
   access said second database for contextual association with data elements previously combined with said exteroceptive values, said reliability metadata and said first metadata;
   assign contextual metadata to said data elements based on contextual associations observed at said second database;
   combine contextual metadata with said exteroceptive values, said reliability metadata and said first metadata; and
   extrapolating from said data elements the probability of a behavioral response based on stimuli potentials necessary for human perception and cognition.

2. The system of claim 1 wherein said first metadata comprises origination data.

3. The system of claim 1 wherein said first metadata comprises temporal data.

4. The system of claim 3 wherein said temporal comprises at least one of date and time data.

5. The system of claim 1 wherein said exteroceptive values comprise sight, smell, hearing, touch, taste, temperature, pressure, pain and pleasure.

6. The system of claim 1 wherein said data harvesting means comprises at least one sensor of analog signals and an analog to digital converter.

7. The system of claim 1 wherein said data harvesting means comprise at least one data scraper.

8. A non-transitory computer readable storage medium with executable programming stored thereon for transforming raw data into data elements having associated exteroceptive values, wherein the program instructs a microprocessor to perform the following steps:
   receive discrete data elements from at least one data harvesting means;
   organize said data elements into at least one data feed;
   assign first metadata to said data elements;
   test data integrity by searching for an alternate number of sources in order to confirm said first metadata;
   access a first database to determine the validity of said data elements based on past data feed metatag usage;
   assign reliability metadata to said data elements;
   combine said reliability metadata with said first metadata;
   assign exteroceptive values to said data elements based on values of said data elements, said reliability metadata and said first metadata;
   combine said exteroceptive values with said reliability metadata and said first metadata;

access a second database for contextual association with data elements previously combined with said exteroceptive values, said reliability metadata and said first metadata;

assign contextual metadata to said data elements based on contextual associations observed at said second database;

combine contextual metadata with said exteroceptive values, said reliability metadata and said first metadata; and extrapolating from said data elements the probability of a behavioral response based on stimuli potentials necessary for human perception and cognition.

9. The storage medium of claim 8 wherein said first metadata comprises origination data.

10. The storage medium of claim 8 wherein said first metadata comprises temporal data.

11. The storage medium of claim 10 wherein said temporal comprises at least one of date and time data.

12. The storage medium of claim 8 wherein said exteroceptive values comprise sight, smell, hearing, touch, taste, temperature, pressure, pain, and pleasure.

13. The storage medium of claim 8 wherein said data harvesting means comprises at least one sensor of analog signals and an analog to digital converter.

14. The storage medium of claim 8 wherein said data harvesting means comprise at least one data scraper.

15. A method for transforming raw data into data elements having associated exteroceptive values using a microprocessor coupled to a memory, the memory including executable programming for controlling the microprocessor, the method comprising:

using the executable programming of the memory to instruct the microprocessor to:

receive discrete data elements from at least one data harvesting means;

organize said data elements into at least one data feed;

assign first metadata to said data elements;

test data integrity by searching for an alternate number of sources in order to confirm said first metadata;

access a first database to determine the validity of said data elements based on past data feed metatag usage;

assign reliability metadata to said data elements;

combine said reliability metadata with said first metadata;

assign exteroceptive values to said data elements based on values of said data elements, said reliability metadata and said first metadata;

combine said exteroceptive values with said reliability metadata and said first metadata;

access a second database for contextual association with data elements previously combined with said exteroceptive values, said reliability metadata and said first metadata;

assign contextual metadata to said data elements based on contextual associations observed at said second database;

combine contextual metadata with said exteroceptive values, said reliability metadata and said first metadata; and extrapolating from said data elements the probability of a behavioral response based on stimuli potentials necessary for human perception and cognition.

16. The method of claim 15 wherein said first metadata comprises origination data.

17. The method of claim 15 wherein said first metadata comprises temporal data.

18. The method of claim 17 wherein said temporal comprises at least one of date and time data.

19. The method of claim 15 wherein said exteroceptive values comprise sight, smell, hearing, touch, taste, temperature, pressure, pain, and pleasure.

20. The method of claim 15 wherein said data harvesting means comprises at least one sensor of analog signals and an analog to digital converter.

21. The method of claim 15 wherein said data harvesting means comprise at least one data scraper.

* * * * *